United States Patent [19]

Kihara et al.

[11] 4,412,011

[45] Oct. 25, 1983

[54] POLYMERIC CHOLESTEROL REDUCING AGENT HAVING VINYLIMIDAZOLE PENDANT GROUPS

[75] Inventors: Kunio Kihara; Hideo Toda; Motokuni Mori; Koji Sato, all of Amimachi, Japan

[73] Assignees: Mitsubishi Petrochemical Co., Ltd.; Mitsubishi Yuka Pharmaceutical Co., Ltd., both of Tokyo, Japan

[21] Appl. No.: 311,069

[22] Filed: Oct. 13, 1981

[30] Foreign Application Priority Data

Mar. 2, 1981 [JP] Japan ............................. 56-28378

[51] Int. Cl.³ .................... B01J 39/20; C08F 26/06; A61K 31/785
[52] U.S. Cl. .................................... 521/38; 526/258; 424/79
[58] Field of Search ............... 521/25, 38; 424/79; 525/375; 526/258

[56] References Cited

U.S. PATENT DOCUMENTS 4,198,395 4/1980 DeSimone ..................... 526/336
4,202,944 5/1980 Hancock et al. .................. 54/32
4,247,648 1/1981 Komboro .................... 525/333.4

OTHER PUBLICATIONS

Chem. Abstracts, vol. 94, 1981, 112468F, Fuji Photo Film, Ltd.
Chem. Abstracts, vol. 84, 53960d, Bazgolev et al.

*Primary Examiner*—Joseph L. Schofer
*Assistant Examiner*—Peter F. Kulkosky
*Attorney, Agent, or Firm*—Frishauf, Holtz, Goodman & Woodward

[57] ABSTRACT

There is provided a cholesterol reducing agent which contains as an active ingredient an anion exchange resin having a functional group of an imidazolium salt represented by the formula:

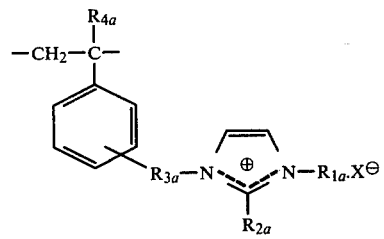

wherein the substituents $R_{1a}$ through $R_{4a}$ and $X^{\ominus}$ are as defined in the specification and claims.

The cholesterol reducing agent according to the present invention has a high selectivity for the adsorption of bile acids and has no bad smell.

12 Claims, No Drawings

POLYMERIC CHOLESTEROL REDUCING AGENT HAVING VINYLIMIDAZOLE PENDANT GROUPS

The present invention relates to a cholesterol reducing agent. Particularly, this invention relates to a cholesterol reducing agent which contains as an active ingredient an anion exchange resin having a functional group of an imidazolium salt.

It is already known to use an anion exchange resin as a so-called cholesterol reducing agent for lowering the level of cholesterol in blood. (Cholestyramine; U.S. Pat. No. 3,499,960 and No. 3,780,171, U.K. Pat. No. 929,391, Japanese Laid-Open Patent Application No. 10386/78). The mechanism whereby the level of cholesterol in blood is lowered by taking the anion exchange resin is considered to be as follows. Namely, the anion exchange resin adsorbs and fixes bile acids in the intestinal tract to prevent the circulation of the bile acids, and cholesterol which is in an equilibrium relation with bile acids, is thereby converted to bile acids, whereby the cholesterol in blood is reduced.

Typical basic anion exchange resins which have hitherto been used as cholesterol reducing agents, are ion exchange resins having a functional group of an aliphatic quaternary ammonium salt (U.S. Pat. Nos. 3,499,960 and No. 3,780,171). The ion exchange resins having a functional group of an aliphatic quaternary ammonium salt can be prepared by reacting an aliphatic tertiary amine to a haloalkyl group introduced to a cross linked polymer. However, the anion exchange resin thereby obtained has a bad smell typical to an aliphatic amine, and cannot therefore be used by itself for a practical application. Therefore, for a practical use, it is common to apply a coating on the surface of the anion exchange resin to reduce the bad smell. However, due to a decrease in the ion exchange capacity by the coating, it is obliged to increase the amount of the dosage. Further, the conventional anion exchange resins have a drawback that they have a low selectivity for the adsorption of bile acids in the presence of inorganic ions.

It is an object of the present invention to provide a cholesterol reducing agent consisting essentially of a basic anion exchange resin which has a high selectivity for the adsorption of bile acids and which has no bad smell.

The basic anion exchange resin which is used as the essential component of the cholesterol reducing agent of the present invention, is a water insoluble anion exchange resin composed of: from 10 to 98 mole % of a structural unit represented by the formula A

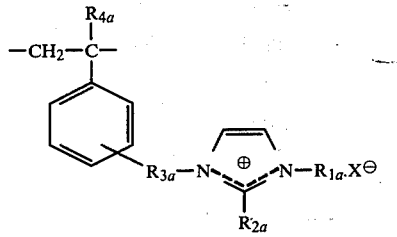

where $R_{1a}$ is an alkyl group of from 1 to 12 carbon atoms, an aryl group of from 6 to 8 carbon atoms, an aralkyl group of 7 or 8 carbon atoms, or a —CH$_2$CH(OH)CH$_2$Cl group; $R_{2a}$ is a hydrogen atom, an alkyl group of from 1 to 17 carbon atoms, an aryl group of from 6 to 8 carbon atoms, or of from 1 to 3 carbon atoms, an alkylene carbonyl group of 2 or 3 carbon atoms, or a carbonyl group; $R_{4a}$ is a hydrogen atom, a methyl group or an ethyl group; and $X^\ominus$ is a halogen ion, a hydroxyl ion or ½ (sulfate ion), from 0 to 90 mole % of a structural unit represented by the formula B

where $R_{1b}$ is a hydrogen atom, a methyl group or an ethyl group; $R_{2b}$ is an aryl group of from 6 to 8 carbon atoms, a

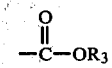

(where $R_3$ is a hydrogen atom, an alkyl group of from 1 to 6 carbon atoms or a glycidyl group), or an acyloxyl group, and from 0.1 to 30 mole % of a structural unit represented by the formula C

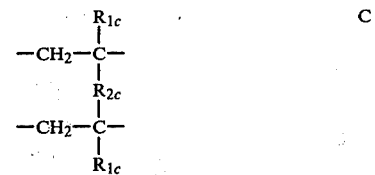

where $R_{1c}$ is a hydrogen atom, or a methyl group; $R_{2c}$ is an arylene group of from 6 to 8 carbon atoms, an alkylene group of from 1 to 12 carbon atoms, or a $$-\overset{O}{\underset{\|}{C}}-O-(CH_2CH_2O)_n-\overset{O}{\underset{\|}{C}}-$$

group (where n is an integer of from 1 to 8).

In the above anion exchange resin, the monomer which gives the structural unit represented by the formula A, plays the most important role for accomplishing the object of the present invention.

The substituents $R_{1a}$, $R_{2a}$, $R_{3a}$, $R_{4a}$ and $X^\ominus$ in the structural unit represented by the formula A are as defined above. Specifically, $R_{1a}$ is an alkyl group of from 1 to 12 carbon atoms such as methyl, ethyl, propyl, butyl, pentyl, hexyl, or dodecyl; an aryl group of from 6 to 8 carbon atoms such as phenyl, tolyl, or xylyl; an aralkyl group of 7 or 8 carbon atoms such as benzyl or phenethyl; or a —CH$_2$CH(OH)CH$_2$Cl group.

$R_{2a}$ is a hydrogen atom; an alkyl group of from 1 to 17 carbon atoms such as methyl, ethyl, propyl, butyl, hexyl, decyl, dodecyl, pentadecyl or heptadecyl; an aryl group of from 6 to 8 carbon atoms such as phenyl, tolyl or xylyl; or an aralkyl group of 7 or 8 carbon atoms such as benzyl or phenethyl.

$R_{3a}$ is an alkylene group of from 1 to 3 carbon atoms such as methylene, ethylene, or propylene; an alkylene carbonyl group of 2 or 3 carbon atoms such as methylene carbonyl or ethylene carbonyl; or a carbonyl group.

$X^\ominus$ is a halogen ion such as an iodine ion, a bromine ion, or a chlorine ion; a hydroxyl ion; or ½ (sulfate ion).

The substituents $R_{1b}$ and $R_{2b}$ in the structural unit represented by the formula B are as defined above. Specifically, $R_{2b}$ is an aryl group of from 6 to 8 carbon atoms such as phenyl, tolyl, or xylyl; a

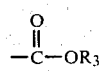

group (where $R_3$ is a hydrogen atom, an alkyl group of from 1 to 6 carbon atoms, or a glycidyl group) such as carboxyl, methoxy carbonyl, ethoxy carbonyl, propoxy carbonyl, butoxy carbonyl, pentyloxy carbonyl, hexyloxy carbonyl, or glycidyl carbonyl; or an acyloxy group.

The substituents $R_{1c}$ and $R_{2c}$ in the structural unit represented by the formula C are as defined above. Specifically, $R_{2c}$ is an arylene group of from 6 to 8 carbon atoms such as phenylene, tolylene or xylene; an alkylene group of from 1 to 12 carbon atoms such as methylene, ethylene, trimethylene, tetramethylene, pentamethylene, heptamethylene, decamethylene or dodecamethylene; or a

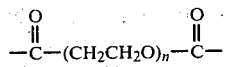

group (where n is an integer of from 1 to 8) such as

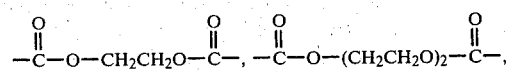

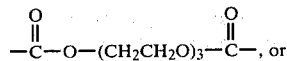, or

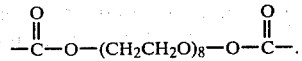.

The polymer substance constituting the anion exchange resin specified by these substituents is cross linked so that it is water insoluble.

Preferred specific anion exchange resins to be used for the present invention are as follows:

tions of Japanese Laid Open Patent Application No. 151682/77 and Japanese Patent Application No. 50404/79 (Anion Exchange Resins and Process of Their Production) previously filed by the present inventors. Namely, the anion exchange resin having a functional group of an imidazolium salt can be produced by introducing an imidazole to a crosslinked polymer.

The polymer is a cross linked resin prepared to have a group reactive with an imidazoles.

As the group reactive with an imidazole, there may be mentioned a haloalkyl group or an acid halide group.

As one of methods for producing a cross linked polymer having such a functional group (which may be called as "functional cross linked polymer"), there may be mentioned a method in which a styrene monomer having a desired functional group (which may be referred to as "functional monomer") is subjected to radical polymerization or other chain polymerization together with a cross linkable monomer and, if necessary, together with other ethylenically unsaturated monomers. The polymerization process per se may be any optional one known to those skilled in the art. Sspecifically, the process may be carried out, for instance, by an emulsion polymerization or a suspension polymerization or the like with use of a peroxide or an azo compound as the radical polymerization initiator. As the monomer having a functional group, there may be mentioned a haloalkyl styrene (as the halogen atom, chlorine, bromine or iodine is suitable, and as the alkyl group, an alkyl group of from 1 to 3 carbon atoms is suitable) such as chloromethyl styrene or bromomethyl styrene.

As the non-cross linkable ethylenically unsaturated monomers which are copolymerizable with such a functional monomer and a cross linkable monomer, there are aromatic vinyl compounds such as styrene, a ring-substituted or side-chain substituted methyl styrene (for instance, α-methyl styrene, vinyltoluene or vinylxylene), alkyl esters of acrylic acid (the alkyl group having from 1 to 6 carbon atoms); alkyl esters of methacrylic acid (the alkyl group having from 1 to 8 carbon atoms); glycidyl ester of methacrylic acid; vinyl acetate; and one or more other kinds.

As the cross linkable monomer, monomers having at least two ethylenically unsaturated bonds are suitable.

| Resin Nos. | Ratios of Monomers (% by weight) | | | | | | Imidazoles (Quarternary agents) | $X^\ominus$ |
|---|---|---|---|---|---|---|---|---|
| | Monomer | Ratio | Monomer | Ratio | Monomer | Ratio | | |
| CR-1 | CMS | 60 | ST | 39.5 | DVB | 0.5 | 1,2-dimethyl imidazole | $Cl^\ominus$ |
| CR-2 | " | " | " | 38 | " | 2 | " | " |
| CR-3 | " | " | " | 36 | " | 4 | " | " |
| CR-4 | " | " | " | 38 | " | 2 | 1-benzyl-2-methyl imidazole | " |
| CR-5 | " | " | " | " | " | " | 1-ethyl-2-undecyl imidazole | $SO_4^\ominus$ |
| CR-6 | " | 30 | " | 68 | " | " | 1,2-dimethyl imidazole | $Cl^\ominus$ |
| CR-7 | " | 75 | " | 23 | " | " | " | " |
| CR-8 | " | 60 | " | 38 | EG | " | " | " |
| CR-9 | " | " | MMA | " | DVB | " | " | " |
| CR-10 | " | " | HA | " | " | " | " | $OH^\ominus$ |
| CR-11 | " | 75 | " | 0 | " | 25 | Imidazole (epichlorohydrin) | $Cl^\ominus$ |
| CR-12 | " | 85 | " | 0 | " | 15 | Imidazole (epichlorohydrin) | " |

CMS: chloromethyl styrene
ST: styrene
DVB: divinyl benzene
EG: diethylene glycol dimethacrylate
MMA: methyl methacrylate
HA: 2-ethylhexyl acrylate Anion exchange resins having a functional group of an imidazolium salt according to the present invention can be prepared by the methods disclosed in the specifica- Specifically, there may be mentioned, for instance, divinyl benzene, trivinyl benzene, divinyl toluene, divinyl xylene, ethylene glycol diacrylate, ethylene glycol dimethacrylate, diethylene glycol diacrylate, diethylene glycol dimethacrylate, and other polyethylene acrylates or methacrylates.

The cross linked copolymer of the present invention can take two different forms. It may be formed into a porous resin either by carrying out the polymerization in the presence of an extractable substance or by carrying out the polymerization in a poor solvent for the polymer. The porous type is suitable particularly for a resin having a high content of the cross linkable monomer at a level of from 2 to 30 mole %, preferably from 12 to 20 mole %. In this case, the water content becomes to be from 50 to 65% by weight.

On the other hand, in a case where no such a porosity treatment is carried out, the resin is used in a gelled form. In this case, the content of the cross linkable monomer is from 0.1 to 10 mole %, preferably from 0.3 to 5.0 mole %. In this case, the water content becomes to be from 65 to 90 mole %.

The ratio of the three components, i.e. the functional monomer, the non-functional monomer and the cross linkable monomer, is 10 to 98: 0 to 90: 0.1 to 30, preferably 20 to 92: 10 to 80: 0.3 to 20, and more preferably 20 to 92: 10 to 80: 0.5 to 20 (in mole ratio).

Another method for producing the cross linked polymer having the functional group is such that in the above mentioned method, instead of the functional monomer, a monomer having a group convertible to the functional group is used. In this case, as the group convertible to the functional group, a carboxylic acid ester group may be mentioned. After the polymerization, such a group may be converted to an acid halide group, one of the functional groups, by hydrolysis or acid halogenation.

A further method for the production of a functional cross-linked polymer is such that a cross linked polymer having no functional group is preliminarily prepared and then a functional group is introduced thereto. For instance, a copolymer of styrene and divinyl benene is reacted with chloromethyl ether to introduce a chloromethyl group thereto by a known method.

Imidazoles to be used for reacting with the above mentioned cross linked polymers having a functional group, are represented by the following general formula

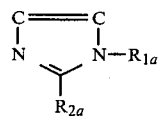

where $R_{1a}$ is an alkyl group of from 1 to 12 carbon atoms, an aryl group of from 6 to 8 carbon atoms, or an aralkyl group of 7 or 8 carbon atoms; $R_{2a}$ is a hydrogen atom, an alkyl group of from 1 to 17 carbon atoms, an aryl group of from 6 to 8 carbon atoms, or an aralkyl group of 7 or 8 carbon atoms.

The aryl group is usually phenyl, tolyl or xylyl. Specific examples of such imidazoles are as follows: 1-methyl imidazole, 1-ethyl imidazole, 1-propyl imidazole, 1,2-dimethyl imidazole, and 1-benzyl-2-methyl imidazole.

Amination Reaction of the Cross Linked Polymer by the Imidazole

The reaction of the cross linked polymer having a haloalkyl group with a 1-substituted imidazole, is conducted by heating both of them in a solvent. Their amounts are suitably selected so that the amount of the imidazole becomes to be at least 0.5 mole relative to the haloalkyl group in the cross linked polymer to be reacted therewith. There is no particular restriction to the reaction temperature. However, the reaction rate is generally high when the temperature is high, and accordingly, it is preferred to choose a temperature of at least 50° C. (the upper limit is about 200° C.).

As the solvent to be used as a reaction medium, an optional one can be chosen which is capable of dissolving the given imidazole. Specifically, methanol, ethanol, butanol, dioxane, tetrahydrofuran, dimethylformamide, or dimethyl sulfoxide may be mentioned. These represent typical examples of good solvents for the imidazoles. However, the solubility may be adjusted by incorporating thereto a poor solvent or a non-solvent for the imidazoles. After the completion of the reaction, the product is filtered and washed by a proper method to obtain the desired resin. Namely, an imidazole having the above mentioned general formula wherein $R_{1a}$ is H is bonded to a cross linked polymer and then the imidazole ring is modified with an epihalohydrin or an alkyl halide to form an imidazolium salt.

The introduction of the imidazole to the cross linked polymer may also be carried out by the following method, other than the above mentioned method. Namely, an imidazole having the above mentioned general formula wherein $R_{1a}$ is H, is bonded to a cross linked polymer and then an alkyl halide having from 1 to 3 carbon atoms or an aralkyl halide having 7 or 8 carbon atoms is added to form an imidazolium salt.

As a specific example, a method may be mentioned in which from 10 to 98% of a haloalkyl styrene, from 0 to 90% of styrene and from 0.1 to 30% of divinyl benzene are polymerized to form a cross linked polymer, whereby an anion exchange resin is obtainable. Alternatively, these monomers in the above mentioned proportion are polymerized in the presence of from 3 to 30% by weight, based on the total weight of the monomers, of noncopolymerizable organic material or in poor solvent for the polymer (such as a solvent containing isooctane, heptane, tert-amyl alcohol, or sec-butanol) to form a porous cross-linked polymer, whereby an anion exchange resin is obtainable. The anion exchange resin thus obtained has the following characteristics:

Ion exchange capacity: 1.0 to 4.0 meq/g. dry resin
Water content: 50 to 90% (g/g wet resin)
Grain size: Passing through a 50 mesh sieve These characteristics were measured by the methods for measurements as described in Example 1 given below.

The essential characteristics of the anion exchange resins having a functional group of an imidazolium salt according to the present invention, are specified in the Test Examples presented hereinafter. It is noted firstly that their bile acid adsorption activity is high (even in the presence of inorganic ions), and secondly that they are odorless.

The selective bile acid adsorption by the imidazolium salt (in the presence of inorganic ions) was found, by the Specifically, there may be mentioned, for instance, divinyl benzene, trivinyl benzene, divinyl toluene, divinyl xylene, ethylene glycol diacrylate, ethylene glycol dimethacrylate, diethylene glycol diacrylate, diethylene glycol dimethacrylate, and other polyethylene acrylates or methacrylates.

The cross linked copolymer of the present invention can take two different forms. It may be formed into a porous resin either by carrying out the polymerization in the presence of an extractable substance or by carrying out the polymerization in a poor solvent for the polymer. The porous type is suitable particularly for a resin having a high content of the cross linkable monomer at a level of from 2 to 30 mole %, preferably from 12 to 20 mole %. In this case, the water content becomes to be from 50 to 65% by weight.

On the other hand, in a case where no such a porosity treatment is carried out, the resin is used in a gelled form. In this case, the content of the cross linkable monomer is from 0.1 to 10 mole %, preferably from 0.3 to 5.0 mole %. In this case, the water content becomes to be from 65 to 90 mole %.

The ratio of the three components, i.e. the functional monomer, the non-functional monomer and the cross linkable monomer, is 10 to 98: 0 to 90: 0.1 to 30, preferably 20 to 92: 10 to 80: 0.3 to 20, and more preferably 20 to 92: 10 to 80: 0.5 to 20 (in mole ratio).

Another method for producing the cross linked polymer having the functional group is such that in the above mentioned method, instead of the functional monomer, a monomer having a group convertible to the functional group is used. In this case, as the group convertible to the functional group, a carboxylic acid ester group may be mentioned. After the polymerization, such a group may be converted to an acid halide group, one of the functional groups, by hydrolysis or acid halogenation.

A further method for the production of a functional cross-linked polymer is such that a cross linked polymer having no functional group is preliminarily prepared and then a functional group is introduced thereto. For instance, a copolymer of styrene and divinyl benene is reacted with chloromethyl ether to introduce a chloromethyl group thereto by a known method.

Imidazoles to be used for reacting with the above mentioned cross linked polymers having a functional group, are represented by the following general formula

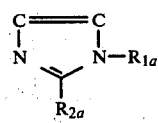

where $R_{1a}$ is an alkyl group of from 1 to 12 carbon atoms, an aryl group of from 6 to 8 carbon atoms, or an aralkyl group of 7 or 8 carbon atoms; $R_{2a}$ is a hydrogen atom, an alkyl group of from 1 to 17 carbon atoms, an aryl group of from 6 to 8 carbon atoms, or an aralkyl group of 7 or 8 carbon atoms.

The aryl group is usually phenyl, tolyl or xylyl. Specific examples of such imidazoles are as follows: 1-methyl imidazole, 1-ethyl imidazole, 1-propyl imidazole, 1,2-dimethyl imidazole, and 1-benzyl-2-methyl imidazole.

Amination Reaction of the Cross Linked Polymer by the Imidazole

The reaction of the cross linked polymer having a haloalkyl group with a 1-substituted imidazole, is conducted by heating both of them in a solvent. Their amounts are suitably selected so that the amount of the imidazole becomes to be at least 0.5 mole relative to the haloalkyl group in the cross linked polymer to be reacted therewith. There is no particular restriction to the reaction temperature. However, the reaction rate is generally high when the temperature is high, and accordingly, it is preferred to choose a temperature of at least 50° C. (the upper limit is about 200° C.).

As the solvent to be used as a reaction medium, an optional one can be chosen which is capable of dissolving the given imidazole. Specifically, methanol, ethanol, butanol, dioxane, tetrahydrofuran, dimethylformamide, or dimethyl sulfoxide may be mentioned. These represent typical examples of good solvents for the imidazoles. However, the solubility may be adjusted by incorporating thereto a poor solvent or a non-solvent for the imidazoles. After the completion of the reaction, the product is filtered and washed by a proper method to obtain the desired resin. Namely, an imidazole having the above mentioned general formula wherein $R_{1a}$ is H is bonded to a cross linked polymer and then the imidazole ring is modified with an epihalohydrin or an alkyl halide to form an imidazolium salt.

The introduction of the imidazole to the cross linked polymer may also be carried out by the following method, other than the above mentioned method. Namely, an imidazole having the above mentioned general formula wherein $R_{1a}$ is H, is bonded to a cross linked polymer and then an alkyl halide having from 1 to 3 carbon atoms or an aralkyl halide having 7 or 8 carbon atoms is added to form an imidazolium salt.

As a specific example, a method may be mentioned in which from 10 to 98% of a haloalkyl styrene, from 0 to 90% of styrene and from 0.1 to 30% of divinyl benzene are polymerized to form a cross linked polymer, whereby an anion exchange resin is obtainable. Alternatively, these monomers in the above mentioned proportion are polymerized in the presence of from 3 to 30% by weight, based on the total weight of the monomers, of noncopolymerizable organic material or in poor solvent for the polymer (such as a solvent containing isooctane, heptane, tert-amyl alcohol, or sec-butanol) to form a porous cross-linked polymer, whereby an anion exchange resin is obtainable. The anion exchange resin thus obtained has the following characteristics:

Ion exchange capacity: 1.0 to 4.0 meq/g. dry resin
Water content: 50 to 90% (g/g wet resin)
Grain size: Passing through a 50 mesh sieve These characteristics were measured by the methods for measurements as described in Example 1 given below.

The essential characteristics of the anion exchange resins having a functional group of an imidazolium salt according to the present invention, are specified in the Test Examples presented hereinafter. It is noted firstly that their bile acid adsorption activity is high (even in the presence of inorganic ions), and secondly that they are odorless.

The selective bile acid adsorption by the imidazolium salt (in the presence of inorganic ions) was found, by the measurement of the ion exchange equilibrium coefficients, to be derived from the fact that the resin having a functional group of the imidazolium salt has less affinity to inorganic ions (i.e. phosphoric acid ion) than a resin having a functional group of an aliphatic ammonium salt, and has greater affinity to bile acids.

Now, the acute toxicity of the anion exchange resins of the present invention will be described.

A suspension comprising a 1% tragacanth solution as the dispersing medium, was orally administered to ICR-JCL mice, and $LD_{50}$ values were determined from the death rate upon expiration of one week, whereby $LD_{50}$ was found to be at least 5 g/kg. The dosage of the cholesterol reducing agent of the present invention for an adult, is from 1 to 30 g per day, preferably from 2 to 10 g per day. Normally, the daily dosage is divided into portions to be taken in a few times a day.

For the administration of the cholesterol reducing agent of the present invention to a human body, an oral administration formulation or a suppository is used. The oral administration is preferred. In the case of the oral administration, it is preferably taken before a meal in a state suspended in water or other liquid.

Now, the present invention will be described in further detail with reference to the Examples and Test Examples and the effectiveness thereof will thereby be apparent.

EXAMPLE 1

(i) A homogeneously mixed solution of 60 g (0.4 mole) of chloromethyl styrene, 39.5 g (0.37 mole) of styrene, 0.9 g ($3.7 \times 10^{-3}$ mole) of divinyl benzene (purity: 55%) and 1 g of azobisisobutylonitrile, was introduced into an aqueous solution prepared by dissolving 3 g of sodium chloride, 1.5 g of polyvinyl pyrrolidone (average molecular weight: $3.6 \times 10^4$) and 0.3 g of sodium pyrophosphate in 300 ml of water. This system was sufficiently stirred to disperse the monomers uniformly, and while supplying a nitrogen gas, the reaction was carried out at 80° C. for 6 hours under heating. Co-polymer particles thereby formed was filtered, washed with water and heated to remove the excess solvent and water to dryness. The copolymer thereby obtained was in a form of colourless spherical grains, and the yield was 87 g.

(ii) Then, 50 g of the copolymer thus obtained was introduced, together with 18.9 g (0.2 mole) of 1,2-dimethyl imidazole and 200 ml of ethanol, into a flask equipped with a stirrer and a reflux condenser, and heated at 80° C. for 8 hours. After the reaction, the product was filtered, and the solid product thereby obtained was washed with ethanol. Then, the product was heated and dried, and thereafter pulverized in a ball mill.

The anion exchange resin thereby obtained (hereinafter referred to simply as "CR-1") had the following characteristics:

Ion exchange capacity: 2.9 meq/g dry resin
Water content: 85% (g/g wet resin)
Grain size: passing through a 150 mesh sieve.

The above characteristics were determined according to the following methods:

Ion Exchange Capacity:

A value of a total exchange capacity representing a sum of a neutral salt decomposing capability and a neutral or weak basic capacity.

(a) Neutral salt decomposing capability: About 3 g of the resin was immersed in 100 ml of a 1.0 N NaOH solution for 5 hours and then washed with water until it becomes neutral. After drying under reduced pressure, from 2 to 3 g of the dried resin was accurately weighed (the weight was designated as "A g"), and added thereto was 100 ml of a 0.5 N NaCl solution, and after stirring for 4 hours, the mixture was left to stand still overnight. After filtration under suction, the filtrate is titrated by a 0.1 N HCl solution (the amount of the 0.1 N HCl solution thereby required for the titraton was designated as "B ml").

The neutral salt decomposing capability was calculated by the following formula:

Neutral salt decomposing capability
(meq/g) = B × (titer of the HCl solution)/10A (b) Weak Basic Capacity: The resin remaining on the funnel was placed in 100 ml of a 0.2 N HCl and left to stand still overnight, and thereafter 10 ml of the supernatant solution was titrated with a 0.1 N NaOH solution (the amount of the 0.1 N NaOH solution thereby required for the titration was designated as "C ml"). Further, 10 ml of the above mentioned 0.2 N HCl solution was titrated by a 0.1 N NaOH solution (the amount of the 0.1 N NaOH solution thereby required for the titration was designated as "D ml").

The weak basic capacity was calculated by the following formula:

Neutral or weak basic capacity
(meq/g) = (D−C) × (titer of the NaOH solution)/A

Water Content:

From 5 to 10 g of the anion exchange resin was immersed in pure water for a day and night, and then filtered under suction until a crack appeared on the surface of the resin layer on the funnel, and the weight (Wa) of the water-containing resin was measured. After drying under reduced pressure at 50° C. for 8 hours, the weight (Wb) of the dried resin was measured.

The water content (%) was calculated by the following formula

Water content (%) = (Wa − Wb)/Wa × 100

Grain Size:

The dried resin was pulverized for from 1 to 2 hours by means of a ball mill made by Alfred Flish Co., and the pulverized resin was sieved by an electromagnetic experimental sieve vibrator to obtain grains of a predetermined size (passing through a 150 mesh sieve).

The characteristics of the anion exchange resins obtained by the following Examples were also determined by the above methods of measurements.

EXAMPLE 2

Fifty grams of a copolymer obtained in a manner similar to Example 1 (i) except that 38 g (0.36 mole) of styrene and 3.6 g ($1.5 \times 10^{-2}$ mole) of divinyl benzene were used, was introduced, together with 18.9 g (0.20 mole) of 1,2-dimethyl imidazole and 200 ml of ethanol, into a flask equipped with a stirrer and a reflux condenser, and heated at 80° C. for 8 hours. After the reaction, the product was filtered and the solid product thereby obtained was washed with ethanol, and then dried and pulverized.

The anion exchange resin thus obtained (referred to simply as "CR-2") had the following characteristics.

Ion exchange capacity: 2.9 meq/g dry resin
Water content: 78% (g/g wet resin)
Grain size: passing through a 150 mesh sieve

EXAMPLE 3

(i) A homogeneously mixed solution comprising 60 g (0.4 mole) of chloromethyl styrene, 36 g (0.34 mole) of styrene, and 7.2 g ($3 \times 10^{-2}$ mole) of divinyl benzene, was introduced into an aqueous solution prepared by dissolving 1 g of potassium persulfate, and 1 g of sodium dodecylsulfate in 250 ml of water. This system was sufficiently stirred to homogeneously emulsify the monomers, and while supplying a nitrogen gas, the reaction was carried out by heating at 60° C. for 6 hours. After the polymerization, this emulsion was placed in a $CaCO_3$ aqueous solution to effect salting out. The product was then filtered, washed with water and dried. The copolymer thereby obtained was white powder particles passing through a 325 mesh sieve, and the yield was 98 g.

(ii) Then, 50 g of the copolymer was placed, together with 18.9 g (0.2 mole) of 1,2-dimethyl imidazole and 200 ml of water, in a flask equipped with a stirrer and a reflux condenser, and reacted in a manner similar to Example 1 (ii) for the aftertreatment.

The anion exchange resin thus obtained (referred to simply as "CR-3") had the following characteristics:

Ion exchange capacity: 2.8 meq/g dry resin
Water content: 67% (g/g wet resin)
Grain size: passing through a 325 mesh sieve

EXAMPLE 4

Ten grams of the copolymer obtained by Example 2 was reacted together with 6.7 g (0.04 mole) of 1-benzyl-2-methyl imidazole and 40 ml of ethanol in a manner similar to Example 1 (ii) for the aftertreatment.

The anion exchange resin thus obtained (referred to simply as "CR-4") had the following characteristics:

Ion exchange capacity: 2.7 meq/g dry resin
Water content: 77% (g/g wet resin)
Grain size: passing through a 150 mesh sieve

EXAMPLE 5

Ten grams of the copolymer obtained by Example 2 was reacted together with 9.8 g (0.04 mole) of 1-ethyl-2-undecyl imidazole and 40 ml of ethanol in a manner similar to Example 1 (ii) for the aftertreatment.

The anion exchange resin thus obtained (referred to simply as "CR-5") had the following characteristics:

Ion exchange capacity: 2.2 meq/g dry resin
Water content: 74% (g/g wet resin)
Grain size: passing through a 150 mesh sieve

EXAMPLE 6

Fifty grams of a copolymer obtained in a manner similar to Example 1 (i) except that 30 g (0.2 mole) of chloromethyl styrene, 68 g (0.65 mole) of styrene and 3.6 g ($1.5 \times 10^{-2}$ mole) of divinyl benzene were used, was reacted together with 14.2 g (0.15 mole) of 1,2-dimethyl imidazole and 200 ml of ethanol in a manner similar to Example 1 (ii) for the aftertreatment.

The anion exchange resin thus obtained (referred to simply as "CR-6") had the following characteristics:

Ion exchange capacity: 2.4 meq/g dry resin
Water content: 66% (g/g wet resin)
Grain size: passing through a 150 mesh sieve

EXAMPLE 7

Fifty grams of a copolymer obtained in a manner similar to Example 1 (i) except that 75 g (0.5 mole) of chloromethyl styrene, 23 g (0.22 mole) of styrene and 3.6 g ($1.5 \times 10^{-2}$ mole) of divinyl benzene were used, was reacted together with 23.7 g (0.25 mole) of 1,2-dimethyl imidazole and 200 ml of ethanol in a manner similar to Example 1 (ii) for the after-treatment.

The anion exchange resin thus obtained (referred to simply as "CR-7") had the following characteristics:

Ion exchange capacity: 3.5 meq/g dry resin
Water content: 81% (g/g wet resin)
Grain size: passing through a 150 mesh sieve

EXAMPLE 8

Fifty grams of a copolymer obtained in a manner similar to Example 1 (i) except that 2 g ($8.3 \times 10^{-3}$ mole) of diethylene glycol dimethacrylate was used, was placed together with 18.9 g (0.2 mole) of 1,2-dimethyl imidazole and 200 ml of ethanol, in a flask equipped with a stirrer and a reflux condenser and heated at 80° C. for 8 hours. After the reaction, the product was filtered and the solid product thereby obtained was washed with ethanol, then dried and pulverized.

The anion exchange resin thus obtained (referred to simply as "CR-8") had the following characteristics:

Ion exchange capacity: 2.9 meq/g dry resin
Water content: 80% (g/g wet resin)
Grain size: passing through a 150 mesh sieve

EXAMPLE 9

Fifty grams of a copolymer obtained in a manner similar to Example 1 (i) except that 38 g (0.38 mole) of methyl methacrylate was used, was placed together with 18.9 g (0.2 mole) of 1,2-dimethyl imidazole and 200 ml of ethanol, in a flask equipped with a stirrer and a reflux condenser, and heated at 80° C. for 8 hours. After the reaction, the product was filtered, and the solid product thereby obtained was washed with ethanol, then dried and pulverized.

The anion exchange resin thus obtained (referred to simply as "CR-9") had the following characteristics:

Ion exchange capacity: 2.7 meq/g dry resin
Water content: 74% (g/g wet resin)
Grain size: passing through a 150 mesh sieve

EXAMPLE 10

Fifty grams of a copolymer obtained in a manner similar to Example 1 (i) except that 38 g (0.21 mole) of 2-ethylhexyl acrylate was used, was placed together with 18.9 g (0.2 mole) of 1,2-dimethyl imidazole and 200 ml of ethanol, in a flask equipped with a stirrer and a reflux condenser, and heated at 80° C. for 8 hours. After the reaction, the product was filtered, and the solid product thereby obtained was washed with ethanol, then dried and pulverized.

The anion exchange resin thus obtained (referred to simply as "CR-10") had the following characteristics:

Ion exchange capacity: 2.5 meq/g dry resin
Water content: 70% (g/g wet resin)
Grain size: passing through a 150 mesh sieve

EXAMPLE 11

(i) A homogeneously mixed solution comprising 75 g (0.49 mole) of chloromethyl styrene, 45.5 g (0.19 mole) of divinyl benzene (purity: 55%), 53 g of isooctane and 1 g of azobisisobutylonitrile, was introduced into an aqueous solution prepared by dissolving 3 g of sodium chloride, 1.5 g of polyvinylpyrrolidone (average molecular weight: $3.6 \times 10^4$) and 0.3 g of sodium pyrophosphate in 300 ml of water. This system was sufficiently stirred to disperse the monomers uniformly, and while supplying nitrogen gas, the reaction was carried out by heating at 80° C. for 7 hours. The copolymer thereby obtained was filtered, washed with water, and heated at a high temperature to remove the excess water and isooctane to dryness. The product was translucent spherical particles and the yield was 103 g.

(ii) Then, 20 g of the copolymer thus obtained was placed together with 20 g of imidazole, 3.9 g of sodium hydroxide, 40 g of toluene and 40 g of ethanol, in a flask equipped with a stirrer and a reflux condenser, and heated at 80° C. for 6 hours. The reaction mixture was filtered, and the solid product thereby obtained was washed with water and dried under reduced pressure. (The cross linked polymer thus obtained was designated as "intermediate polymer A").

(iii) Then, 15 g of the intermediate polymer A was placed together with 4.5 g of epichlorohydrin, 30 g of toluene, and 30 g of ethanol, in a flask equipped with a stirrer and a reflux condenser, and heated at 80° C. for 10 hours. The reaction mixture was filtered, and the solid product thereby obtained was washed with methanol, then with a 3% sodium hydroxide solution and a 3% hydrochloric acid solution and finally sufficiently with water. After the washing, the solid product thereby obtained was heated to dryness. The porous anion exchange resin thereby obtained (referred to simply as "CR-11") had the following characteristics:

Ion exchange capacity: 2.2 meq/g
Pore volume: 0.53 cc/g
Average pore diameter: $2 \times 10^2$ Å
Grain size: from 200 to 325 mesh

EXAMPLE 12

(i) Thirty grams of the copolymer obtained in a manner similar to Example 11 (i) except that 85 g (0.56 mole) of chloromethyl styrene and 27.3 g (0.12 mole) of divinyl benzene (purity: 55%) were used, was placed together with 34.1 g of imidazole, 6.7 g of sodium hydroxide, 60 g of toluene, and 60 g of ethanol, in a flask equipped with a stirrer and a reflux condenser, and heated at 80° C. for 6 hours.

The reaction mixture was filtered, and the solid product thereby obtained was washed with water and dried under reduced pressure. (The cross linked copolymer thus obtained was designated as "intermediate polymer B").

(ii) Twenty grams of the intermediate polymer B was placed together with 6.7 g of epichlorohydrin, 40 g of toluene, and 40 g of ethanol, in a flask equipped with a stirrer and a reflux condenser, and heated at 80° C. for 10 hours. The reaction mixture was filtered, and the solid product thereby obtained was washed with methanol, then with a 3% sodium hydroxide solution and a 3% hydrochloric acid solution, and finally sufficiently with water. The solid product thus obtained was heated to dryness.

The porous anion exchange resin thus obtained (referred to simply as "CR-12") had the following characteristics:

Ion exchange capacity: 2.4 meq/g
Pore volume: 0.69 cc/g
Average pore diameter: $5 \times 10^2$ Å
Grain size: from 200 to 325 mesh

TEST EXAMPLE 1

In vitro test (1) In vitro test for adsorption of sodium cholate by various anion exchange resins In each of thirteen Erlenmeyer flasks, 50 ml of a solution containing 0.43 mg/ml of sodium cholate adjusted with use of a phosphoric acid buffer solution (0.25 M, pH 7.5), was introduced, and 50 ml of each of CR-1, 2, 3, 4, 5, 6, 7, 8, 9, 10, 11, 12 and cholestry amine was respectively added thereto. After incubation at 37° C. for 24 hours, the mixture was centrifuged, and the supernatant solution was collected and subjected to a quantitative analysis of the remaining sodium cholate by an enzymatic reaction method (with use of a bile acid concentration measuring reagent (Sterognost-3α) made by Daiichi Pure Chemicals Co. The results thereby obtained are shown in Table 1.

TABLE 1

| Proportions (%) of the fixed sodium cholate | |
|---|---|
| Cholestyramine | 29 |
| CR-1 | 74 |
| CR-2 | 75 |
| CR-3 | 75 |
| CR-4 | 62 |
| CR-5 | 70 |
| CR-6 | 72 |
| CR-7 | 67 |
| CR-8 | 60 |
| CR-9 | 64 |
| CR-10 | 72 |
| CR-11 | 30 |
| CR-12 | 35 |

From the results shown in Table 1, it is apparent that the anion exchange resins of the present invention adsorb a considerable amount of sodium cholate in the phosphoric acid buffer solution.

(2) In vitro test for adsorption of sodium cholate by the resins in cases where the concentration and the kind of the buffer solution were varied.

In each of Erlenmeyer flasks, 30 ml of a solution containing 0.43 mg/ml of sodium cholate adjusted with use of various buffer solutions, was introduced, and 30 mg of each resin of CR-2, 4, 9, 12 and cholestyramine, was further added respectively. The adsorption test was carried out in a manner similar to the method of (1) and the remaining sodium cholate was quantitatively analyzed. The results thereby obtained are shown in Table 2.

TABLE 2

| Buffer solutions | Concentrations (M) | Proportions (%) of the bonded sodium cholate | | | | |
|---|---|---|---|---|---|---|
| | | Cholestyramine | CR-2 | CR-4 | CR-9 | CR-12 |
| Phosphoric acid buffer solution | 0.0 | 90 | 98 | 93 | 94 | 60 |
| Phosphoric acid buffer solution | 0.05 | 23 | 78 | 73 | 75 | 38 |
| Phosphoric acid buffer solution | 0.25 | 29 | 75 | 62 | 64 | 35 |
| Carbonic acid buffer solution | 0.25 | 22 | 65 | 52 | 54 | 33 |

Phosphoric acid buffer solution: potassium dihydrogen-phosphate was used.
Carbonic acid buffer solution: Sodium hydrogen carbonate was used.

From the results shown in Table 2, it is apparent that with the anion exchange resins CR-2, 4, 9 and 12 of the present invention, the dependency of the decrease of the adsorption rate on the concentration of the buffer solution is less in the phosphoric acid buffer solutions, and that they have a high sodium cholate adsorbing capability also in the carbonic acid buffer solution.

Namely, it is seen that the anion exchange resins of the present invention, are capable of selectively adsorbing sodium cholate even in the presence of various inorganic ions.

This indicates that the anion exchange resins of the present invention are extremely useful in the intestinal tracts where various inorganic ions are present.

(3) In vitro test for adsorption of sodium cholate by the resins in cases where the pH was varied.

In each of Erlenmeyer flasks, 30 ml of a solution containing 0.43 mg/ml of sodium cholate adjusted with use of phosphoric acid buffer solutions having various pH values, was introduced, and 30 ml of each resin of CR-2, 4, 9, 12 and cholestyramine, was further added respectively. The adsorption test was carried out in a manner similar to the method of (1), and the remaining sodium cholate was quantatively analyzed. The results thereby obtained are shown in Table 3.

TABLE 3

| Phosphoric acid buffer solution (M) | pH | Proportions (%) of the bonded sodium cholate | | | | |
|---|---|---|---|---|---|---|
| | | Cholestyramine | CR-2 | CR-4 | CR-9 | CR-12 |
| 0.25M | 6.0 | 32 | 73 | 67 | 65 | 36 |
| " | 7.0 | 24 | 70 | 65 | 61 | 34 |
| " | 8.0 | 29 | 74 | 62 | 65 | 35 |

Phosphoric acid buffer solution: Sodium hydrogen phosphate was added in the same amount as specified in Table 3, and then the pH was adjusted by hydrochloric acid or sodium hydroxide.

From the above results, it is apparent that the anion exchange resins of the present invention are highly effective in adsorbing sodium cholate at a pH of from 6 to 8 and at a buffer solution concentration of 0.25 M, i.e. under a condition close to that in vivo (i.e. in the intestinal tracts).

(4) In vitro test for adsorption of various sodium bile acids by the resins

In each of Erlenmeyer flasks, 30 ml of a solution of each of various sodium bile acids (i.e. sodium glycocholate, sodium taurocholate and sodium deoxycholate) having a concentration of 0.43 mg/ml adjusted with use of a phosphoric acid buffer solution (0.25 M, pH 7.5), was placed, and 30 ml of each resin of CR-2, 4, 9, 12 and cholestyramine was further added respectively. The adsorption test was carried out in a manner similar to the method of (1), and the remaining sodium bile acids were quantitatively analyzed. The results thereby obtained are shown in Table 4.

TABLE 4

| Sodium bile acids | Proportions (%) of bonded sodium bile acids | | | | |
|---|---|---|---|---|---|
| | Cholestyramine | CR-2 | CR-4 | CR-9 | CR-12 |
| Sodium glycocholate | 35 | 71 | 63 | 59 | 35 |
| Sodium taurocholate | 45 | 82 | 85 | 76 | 47 |
| Sodium deoxycholate | 85 | 93 | 93 | 91 | 40 |

From the results shown in Table 4, it is apparent that the anion exchange resins of the present invention are highly effective in adsorbing the deoxy type (sodium deoxycholate), the glycine conjugated type (sodium glycocholate) and the taurine conjugated type (sodium taurocholate) which are abundantly present in vivo (i.e. in the intestinal tracts) in addition to sodium cholate.

(5) Ion exchange equilibrium coefficients of the anion exchange resins with phosphoric acid and sodium cholate In an Erlenmeyer flask, 30 mg of a resin of CR-2 or cholestyramine was placed, and 30 ml of a phosphoric acid solution or a sodium cholate solution prepared to bring the concentration to be equivalent to the ion exchange group in the resin, was further added. The mixture was incubated at 37° C. for 24 hours, and then the remaining phosphoric acid or sodium cholate was quantitatively analyzed. Then, the ion exchange equilibrium coefficient K was calculated by the following formula. The results thereby obtained are shown in Table 5.

$$K_{Cl\ominus}^{X\ominus} = \frac{\overline{[X^-]}}{\overline{[Cl^-]}} \cdot \frac{[Cl^-]}{[X^-]}$$

$\overline{[X^-]}, \overline{[Cl^-]}$: Moles of $X^-$ or $Cl^-$ taken into the resin at the time of the ion exchange equilibrium $[X^-], [Cl^-]$: Moles of $X^-$ or $Cl^-$ present in the solution at the time of the ion exchange equilibrium

TABLE 5

| Resin | $K_{Cl\ominus}^{phosphoric\ acid\ominus}$ | $K_{Cl\ominus}^{cholic\ acid\ominus}$ | $K_{phosphoric\ acid\ominus}^{cholic\ acid\ominus}$ |
|---|---|---|---|
| Cholestyramine | 0.45 | 14 | 32 |
| CR-2 | 0.24 | 65 | 271 |

$K_{Phosphoric\ acid\ominus}^{cholic\ acid\ominus} = K_{Cl\ominus}^{cholic\ acid\ominus} / K_{Cl\ominus}^{phosphoric\ acid\ominus}$ From the above results, it is apparent that the anion exchange resin of the present invention (CR-2) has a feature that it has a small affinity to phosphoric acid ions and a great affinity to cholic acid ions, and from the values of $K_{phosphoric\ acid\ominus}^{cholic\ acid\ominus},$ the reason for the high bile acid adsorbing activity of (1) to (4) in Test Example 1 in the presence of phosphoric acid has been made clear.

TEST EXAMPLE 2

In vivo test with use of mice

Male ICR-JOL mice having a weight of 18 g were used in groups each composed of five mice. To the first group of mice, a powder mouse food prepared by Nippon Clea Japan Inc. and mixed with 1% of cholesterol and 0.5% of cow bile powder, was fed in an amount of 2 g per 10 g of the weight a day, and to the second and the third groups of mice, CR-2 resin and cholestyramine resin, were additionally fed, respectively. The resin was mixed with the food in an amount of 2.5% of the food. On the seventh day after the administration of the high cholesterol food and the medicinal, blood was collected from a vein of the fundus of the mice, and a total amount of cholesterol in the centrifuged blood plasma was quantitatively analyzed. The results thereby obtained are shown in Table 6.

TABLE 6

| | Total blood plasma cholesterol (mg/dl) | Inhibition rate (%) |
|---|---|---|
| Control | 105.2 ± 2.1 | 100 |
| 1% cholesterol food | 164.8 ± 5.1 | 0 |
| 1% cholesterol food + cholestyramine | 132.5 ± 5.3** | 54.2 |
| 1% cholesterol food + CR-2 | 108.9 ± 4.9** | 93.8 |

**P < 0.01

From the above data, it is apparent that the anion exchange resin of the present invention is effective to lower the level of cholesterol in vivo.

TEST EXAMPLE 3

In vivo test with use of rabbits

Male Newzealand rabbits having a weight of 2.2 kg were used in groups each composed of from 5 to 7 rabbits. To the first group of the rabbits, a food prepared by Oriental Yeast Co. and containing 0.67% of cholesterol, was fed in an amount of 40 g/kg a day, and to the second and third groups of the rabbits, CR-2 resin and cholestyramine were additionally fed, respectively. The resin was mixed with the food in an amount of 0.5% of the food. On the seventh day after the administration of the high cholesterol food and the medicinal, blood was collected from a vein of the external ears and a total amount of cholesterol in the centrifuged blood plasma was measured by Cholesterol-Test Wako (Wako Pure Chemical Industries). The results thereby obtained are shown in Table 7.

TABLE 7

| | Total blood plasma cholesterol (mg/dl) | Inhibition rate (%) |
|---|---|---|
| Control | 44.0 ± 5.1 | 100 |
| 0.67% cholesterol food | 378.0 ± 33.0 | 0 |
| 0.67% cholesterol food + cholestyramine | 381.3 ± 40.7 | 0 |
| 0.67% cholesterol food + CR-2 | 193.3 ± 37.6** | 55.3 |

**P < 0.01

From the above data, it is apparent that the anion exchange resin of the present invention is effective to lower the level of cholesterol in vivo.

What is claimed is:

1. A cholesterol reducing agent which consists essentially of a water-insoluble anion exchange resin composed of from 10 to 98 mole % of a structural unit represented by the formula A

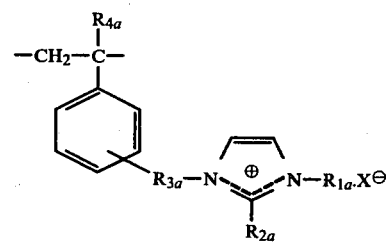

where, $R_{1a}$ is an alkyl group of from 1 to 12 carbon atoms, an aryl group of from 6 to 8 carbon atoms, an aralkyl group of 7 or 8 carbon atoms, or a $-CH_2CH(OH)CH_2Cl$ group; $R_{2a}$ is a hydrogen atom, an alkyl group of from 1 to 17 carbon atoms, an aryl group of from 6 to 8 carbon atoms, or an aralkyl group of 7 or 8 carbon atoms; $R_{3a}$ is an alkylene group of from 1 to 3 carbon atoms; $R_{4a}$ is a hydrogen atom, a methyl group or an ethyl group; and $X^{\ominus}$ is a halogen ion, a hydroxyl ion, or ½ (sulfate ion), from 0 to 90 mole % of a structural unit represented by the formula B

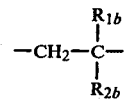

where $R_{1b}$ is a hydrogen atom, a methyl group or an ethyl group; and $R_{2b}$ is an aryl group of from 6 to 8 carbon atoms, a

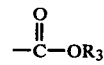

group (where $R_3$ is a hydrogen atom, an alkyl group of from 1 to 6 carbon atoms, or a glycidyl group) or an acryloxyl group, and from 0.1 to 30 mole % of a structural unit represented by the formula C

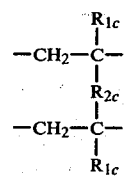

where $R_{1c}$ is a hydrogen atom or a methyl group; $R_{2c}$ is an arylene group of from 6 to 8 carbon atoms, an alkylene group of from 1 to 12 carbon atoms, or a

group (where n=1 to 8).

2. The cholesterol reducing agent as claimed in claim 1, wherein the component C is in an amount of from 0.1 to 10 mole %, and the water content of the resin is from 65 to 90% by weight.

3. The cholesterol reducing agent as claimed in claim 1, wherein the component C is in an amount of from 0.5 to 5.0 mole % and the resin is a gel type having a water content of from 65 to 90% by weight.

4. The cholesterol reducing agent as claimed in claim 1, wherein $R_{2b}$ of the component B is an aryl group of from 6 to 8 carbon atoms, and $R_{2c}$ of the component C is an arylene group of from 6 to 8 carbon atoms.

5. The cholesterol reducing agent as claimed in claim 4, wherein $R_{2b}$ of the component B is a phenyl group, and $R_{2c}$ of the component C is a phenylene group.

6. The cholesterol reducing agent as claimed in claim 1, wherein the component C is in an amount of from 12 to 20 mole % and the resin is a porous type.

7. The cholesterol reducing agent as claimed in claim 4, wherein the component C is in an amount of from 0.1 to 10 mole %, and the water content of the resin is from 65 to 90% by weight.

8. The cholesterol reducing agent as claimed in claim 5, wherein the component C is in an amount of from 0.1 to 10 mole %, and the water content of the resin is from 65 to 90% by weight.

9. The cholesterol reducing agent as claimed in claim 4, wherein the component C is in an amount of from 0.5 to 5.0 mole % and the resin is a gel type having a water content of from 65 to 90% by weight.

10. The cholesterol reducing agent as claimed in claim 5, wherein the component C is in an amount of from 0.5 to 5.0 mole % and the resin is a gel type having a water content of from 65 to 90% by weight.

11. The cholesterol reducing agent as claimed in claim 4, wherein the component C is in an amount of from 12 to 20 mole % and the resin is a porous type.

12. The cholesterol reducing agent as claimed in claim 5, wherein the component C is in an amount of from 12 to 20 mole % and the resin is a porous type.

* * * * *